(12) United States Patent (10) Patent No.: US 6,356,346 B1
Hagen et al. (45) Date of Patent: Mar. 12, 2002

(54) DEVICE AND METHOD FOR INSPECTING A DISK FOR PHYSICAL DEFECTS

(75) Inventors: John Patrick Hagen, Rochester; Daniel A. Neseth, Byron, both of MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/489,342

(22) Filed: Jan. 21, 2000

(51) Int. Cl.[7] .......................... G01N 21/00; G01N 21/86
(52) U.S. Cl. .......................... 356/237.1; 356/237.5; 356/237.6; 250/559.01; 250/559.42
(58) Field of Search .......................... 356/237.1, 237.5, 356/237.6, 239.7, 239.8, 445, 446, 432–435, 376; 250/559.01, 559.11, 559.16, 559.4, 559.41, 559.42, 559.45; 364/550, 551.01, 552; 414/416, 417, 331, 433, 757, 776

(56) References Cited

U.S. PATENT DOCUMENTS

| | | | | |
|---|---|---|---|---|
| 4,423,331 A | * | 12/1983 | Koizumi et al. | 250/572 |
| 4,892,455 A | * | 1/1990 | Hine | 414/417 |
| 4,896,278 A | * | 1/1990 | Grove | 364/552 |
| 5,135,303 A | * | 8/1992 | Uto et al. | 356/237.1 |
| 5,448,364 A | * | 9/1995 | Moran | 356/430 |
| 5,715,051 A | * | 2/1998 | Luster | 356/239.1 |
| 5,914,495 A | * | 6/1999 | Ishizuka et al. | 250/559.45 |
| 6,062,084 A | * | 5/2000 | Chang et al. | 73/601 |
| 6,067,154 A | * | 5/2000 | Hossain et al. | 356/237.2 |
| 6,097,482 A | * | 8/2000 | Smith et al. | 356/237.1 |

* cited by examiner

Primary Examiner—Frank G. Font
Assistant Examiner—Michael P. Stafira
(74) Attorney, Agent, or Firm—Freling E. Baker; Lawrence A. Maxham (57) ABSTRACT

A device and associated method useful for determining whether a disk has a chipped edge. The preferred device includes a laser that radiates a laser beam to the disk in the vicinity of its edge. The preferred device also includes a radiation detector for detecting electromagnetic radiation from the laser after the radiation has been transmitted, reflected, retracted or scattered by the disk. A chip in the vicinity of the edge of the disk will direct the electromagnetic radiation differently than an intact disk edge. Therefore, the radiation detector can utilize changes in the detected electromagnetic radiation in order to determine whether the edge of the disk is intact or whether it has a defect, such as an edge chip.

20 Claims, 8 Drawing Sheets

DEVICE AND METHOD FOR INSPECTING A DISK FOR PHYSICAL DEFECTS

BACKGROUND OF THE INVENTION

1. Field of the Invention

The present invention relates to inspection of a disk for defects, such as chips at the circumferential edges of the disk. More specifically, the present invention relates to inspection of a transparent disk, to be used in constructing a computer storage medium, using a laser beam.

2. Background

Digital data is often stored on a disk. For example, personal computers generally have at least one built-in disk (sometimes called a hard drive) to store digital computer data. As another example, compact disc players and DVD players read and display audio and or visual data from disks. In these applications, even a small physical defect, such as a small chip at the edge of the disk, can cause problems in reading digital data from or writing digital data to the disk.

In response to this recognized problem of physical defects at the edge of disk, disk manufacturers conventionally have a person visually inspect the edge of each disk for chips or other defects.

Although manufacturers have used laser beams to inspect the surface of a disk, these conventional inspection devices do not inspect the edge of the disk for edge chipping, largely because any data in the vicinity of the edge of the disk is used to: (1) exactly locate the disk in space with respect to the inspection device, and (2) provide baseline laser intensity data for normalizing and interpreting laser intensity data measured at locations away from the edge of the disk.

Because the data from the vicinity of the disk edge is used for disk-location and intensity calibration purposes, this data cannot be used by conventional inspection devices to determine whether defects exist at a disk's circumferential edges. These conventional inspection machines do not generally inspect for physical defects closer than 1 mm to the circumferential edge or circumferential chamfer of the disk.

SUMMARY OF THE INVENTION

According to a primary aspect of the present invention, a disk inspection device for inspecting the circumferential edge of a disk includes a beam generator, a disk holder and a radiation detector. The beam generator generates a beam of electromagnetic radiation. The disk holder holds the disk, so that the beam will intersect the disk at an intersection zone, with the intersection zone being sufficiently close to the circumferential edge so that at least a portion of the intersection zone will overlap at least a portion of any defect in the disk. The radiation detector detects at least a portion of radiation from the beam after the beam has intersected the disk. This detected radiation can be used to determine whether the disk edge is intact and correctly shaped.

As used herein, the word "defect" means any irregularity that yields a disk unsuitable for commercial use.

BRIEF DESCRIPTION OF THE DRAWINGS

The above and other object and advantages of the present invention will become apparent from the following description when read in conjunction with the accompanying drawings wherein.

DETAILED DESCRIPTION OF THE PREFERRED EMBODIMENT

Manual visual inspection of disk edges is a relatively slow process that can lengthen manufacturing time. Moreover, manual inspection is not perfect and can miss defects that should be detected. Furthermore, using manual inspection can be relatively expensive.

According to the present invention, a beam of electromagnetic radiation is directed to the edge of a disk. Depending on the material the disk is made of, and on the geometry of the disk at the point it is intersected by the beam, the disk will transmit, reflect, scatter, refract and/or diffract the radiation. If the edge of the disk is intact without defect, the disk will transmit, reflect, scatter, refract and/or diffract portions of the beam in a predictable way. Therefore, a radiation detector can be located so that an intact disk will predictably direct a portion of the beam to the radiation detector (by transmission, refraction, reflection, etc.).

However, a physical defect, such as a chip in the edge of the disk or a misshapen disk edge, will change the manner in which the disk directs the beam. In this case, the radiation detector will generally receive more or less radiation than when the edge of the disk is correctly shaped and intact. Therefore, the radiation detector detects a defect in the disk by detecting a change (usually a decrease) in the amount of received electromagnetic radiation.

For example, the smooth surfaces of a transparent glass disk will transmit most of the laser beam onto a visible light detector placed behind the disk. However, if the edge of such a disk were chipped, the irregular surfaces of the chip would cause more of the beam to be scattered and less of the beam to be transmitted to the visible light detector. In this example, a decrease in detected radiation at the detector would signal a chip defect in the vicinity of the circumferential edge of the disk.

Figure 1:
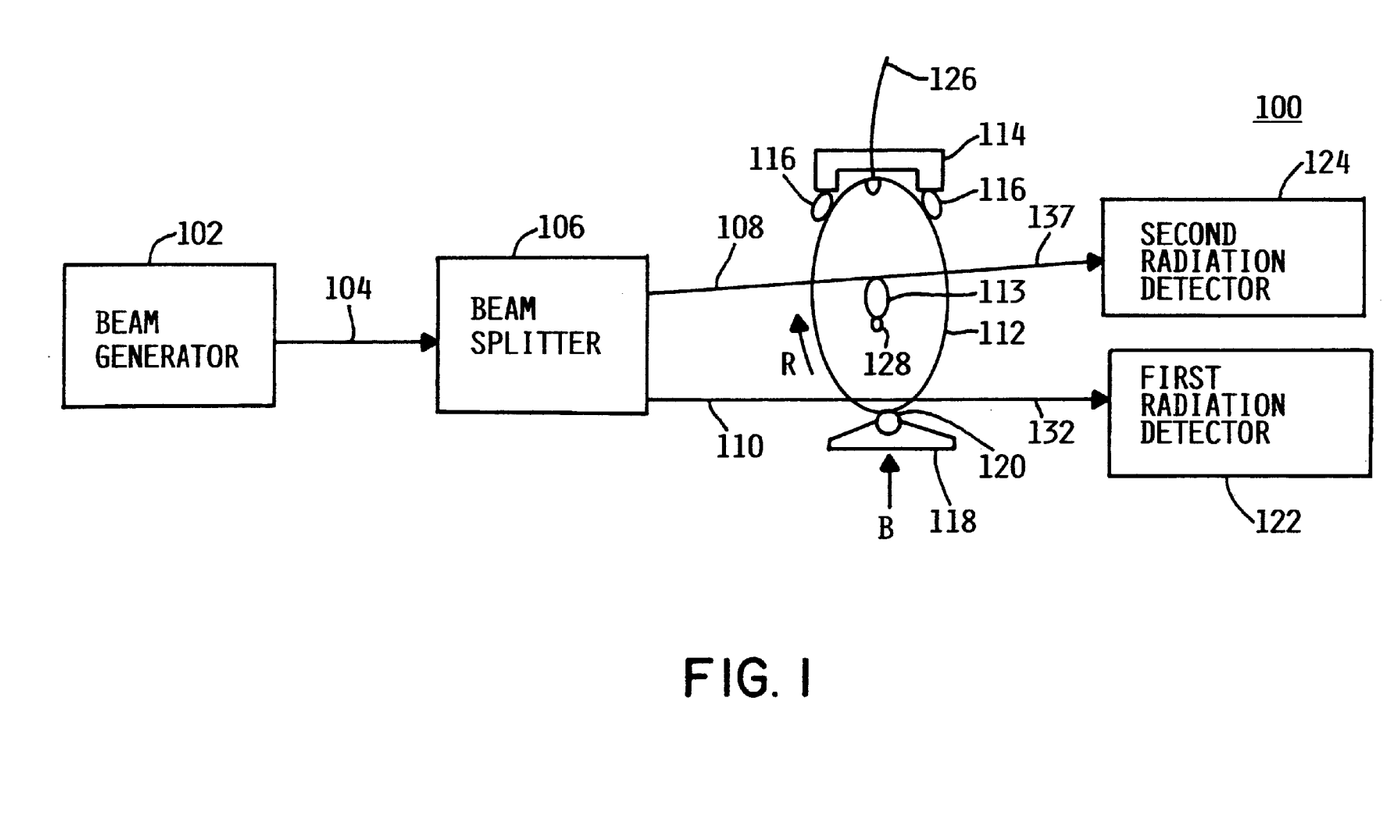
FIG. 1 is a schematic view of a first embodiment of an inspection device according to the present invention.

FIG. 1 shows a first embodiment of a disk inspection device 100 (or edge check machine) according to the present invention. Disk inspection device 100 includes beam generator 102, beam splitter 106, disk holder 114, first radiation detector 122 and second radiation detector 124.

Beam generator 102 generates a beam 104 of electromagnetic radiation, preferably coherent electromagnetic radiation. This beam 104 is directed to beam splitter 106, where the beam is split into two beams: inner beam 108 and outer beam 110. Beams 108 and 110 proceed to the vicinity of disk 112. More particularly, outer beam 110 intersects disk 112 in the vicinity of its outer circumferential edge, while inner beam 108 intersects disk 112 at its inner circumferential edge in the vicinity of central aperture 113.

Because disk 112 shown in FIG. 1 is free of defects, such as edge chips, at the location where beam 110 intersects disk 112, most of the beam 110 is transmitted by the disk 112, such that transmitted beam 132 passes through the disk and proceeds directly to first radiation detector 122. First radiation detector 122 detects transmitted beam 132, and determines, based on the relatively strong received signal, that there is not a defect in the portion of the outer circumferential edge of disk 112 that is intersected by outer beam 110. First radiation detector 122 may include a computer, such as a dedicated personal computer in order to evaluate whether the received radiation indicates the presence of a defect.

Similarly, inner beam 108 is transmitted through the vicinity of an intact portion of the inner circumferential edge of disk 112, and proceeds as transmitted beam 130 to second radiation detector 124. Because second radiation detector 124 receives a relatively large amount of electromagnetic radiation, it is determined that the inner circumferential edge of disk 112 is intact at the location where it is intersected by inner beam 108. Second radiation detector 124 may include a computer, for evaluating the inner edge for defects. Preferably, first and second radiation detectors 122, 124 would share any necessary computer.

If disk 112 were stationary, then beams 108 and 110 could only be used to detect defects at single points on the inner and outer circumferential edges of disk 112. More comprehensive inspection of the entire edges of the disk could be accomplished by using a beam large enough to overlap the entire edges of the disk, although this solution may be somewhat difficult to achieve in practice. More preferably, the entire circumferential edges of the disk can be inspected by moving the beams and/or disk relative to each other. For example, beams 108 and 110 can be scanned around the edges of the disk by a moving beam generator or moving mirrors.

Figure 2:
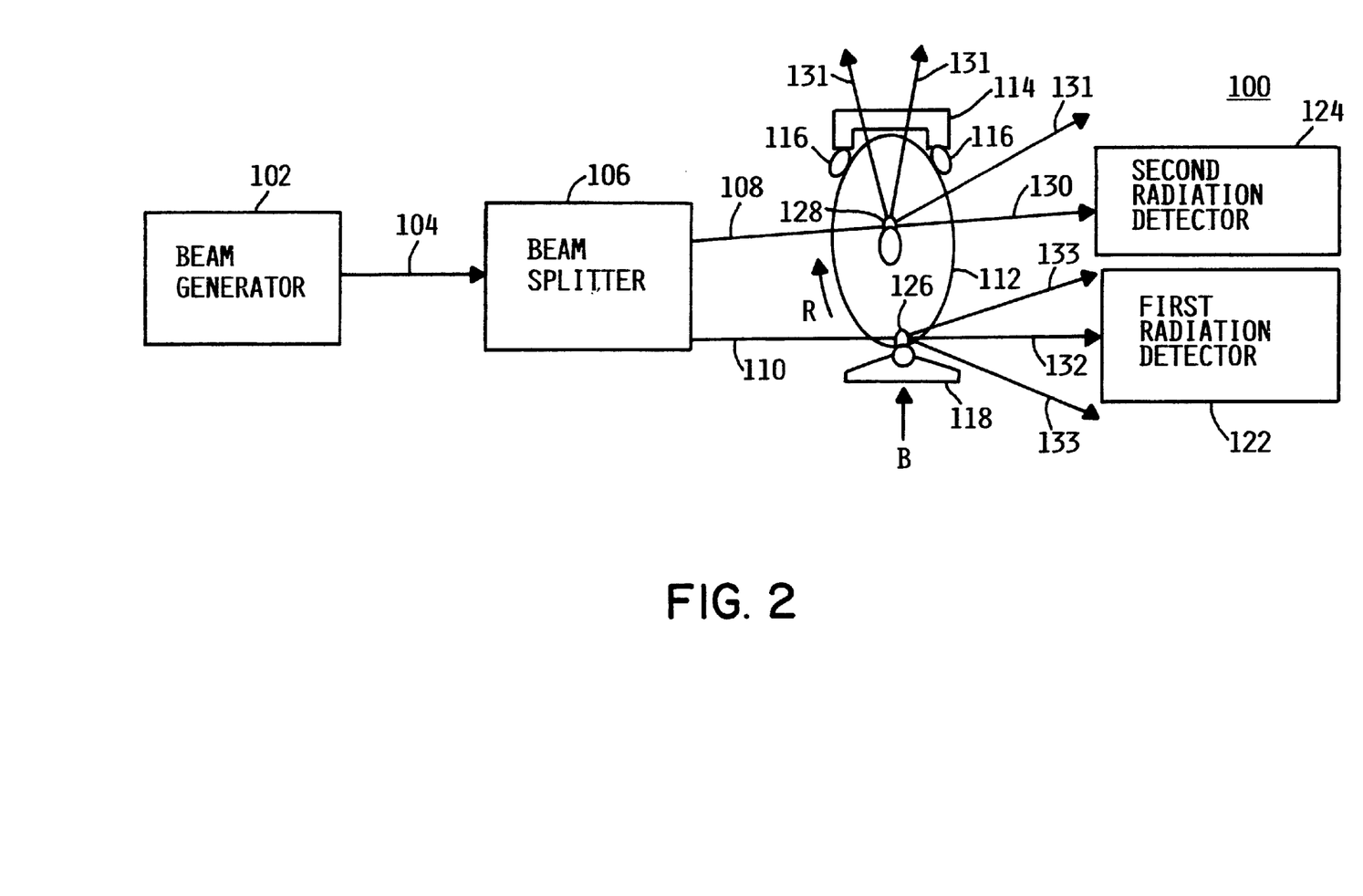
FIG. 2 shows the first embodiment of FIG. 1 at a time when the beams of the inspection device are partially scattered by defects in the circumferential edge of a disk.

In a preferred disk inspection device 100, inner beam 108 an outer beam 110 remain substantially stationary, while disk 112 is rotated in the direction indicated by arrow R. As shown in FIGS. 1 and 2, the outer circumferential edge of disk 112 has chip 126, while inner circumferential edge of disk 112 has chip 128. In FIG. 1, the disk is oriented so that beams 108 and 110 do not intersect defects 126, 128, respectively.

However, as shown in FIG. 2, when disk 112 is rotated in the direction of arrow R so that defect 126 comes into intersection with outer beam 110, defect 126 does transmit some electromagnetic radiation as transmitted beam 132, but a large portion of outer beam 110 is also scattered as shown by vector arrows 133. Because a large portion of outer beam 110 is scattered, transmitted beam 132 is decreased relative to its strength when transmitted by an intact portion of the outer circumferential disk edge. In this way, defect 126 causes a decrease in radiation received by first radiation detector 122, and defect 126 is indicated.

As also shown in FIG. 2, defect 128 has been rotated into intersection with inner beam 108. Defect 128 scatters a portion of inner beam 108 as shown by vector arrows 131, so that a decreased transmitted beam 130 is received by second radiation detector 124. This decrease in radiation received by second radiation detector 124 indicates the presence of defect 128 in the inner circumferential edge of disk 112.

Disk holder 114 is used to hold and rotate disk 112 relative to beams 108, 110. Disk holder 114 includes drive wheels 116, biased arm 118 and idler wheel 120. Biased arm 118 is biased in the direction indicated by arrow B, thereby pressing idler wheel 120 up against the outer circumferential edge of disk 112 to firmly secure disk 112 between idler wheel 120 and drive wheels 116. Drive wheels 116 are driven by a motor (not shown). Consequently, disk 112 is driven to rotate by friction at the rolling points of contact between drive wheels 116 and disk 112. Idler wheel 120 is free to rotate under the influence of rotating disk 112. Alternatively, other type of mechanisms, such as rotating spindles, can be used to hold the disk and drive it.

Figure 3:
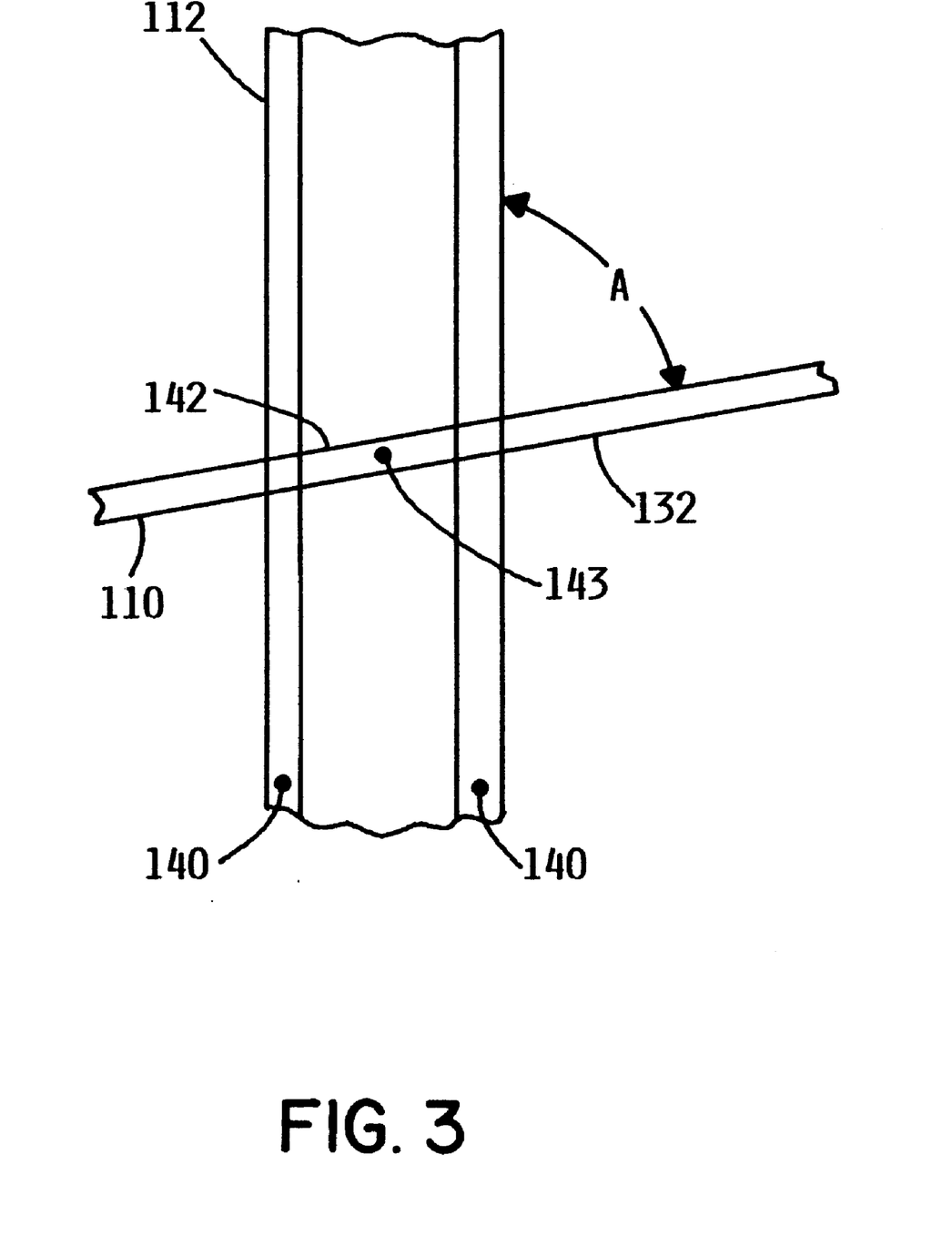
FIG. 3 is a bottom view of an edge portion of a disk transmitting a beam from the first embodiment of the inspection device of FIG. 1.
Figure 4:
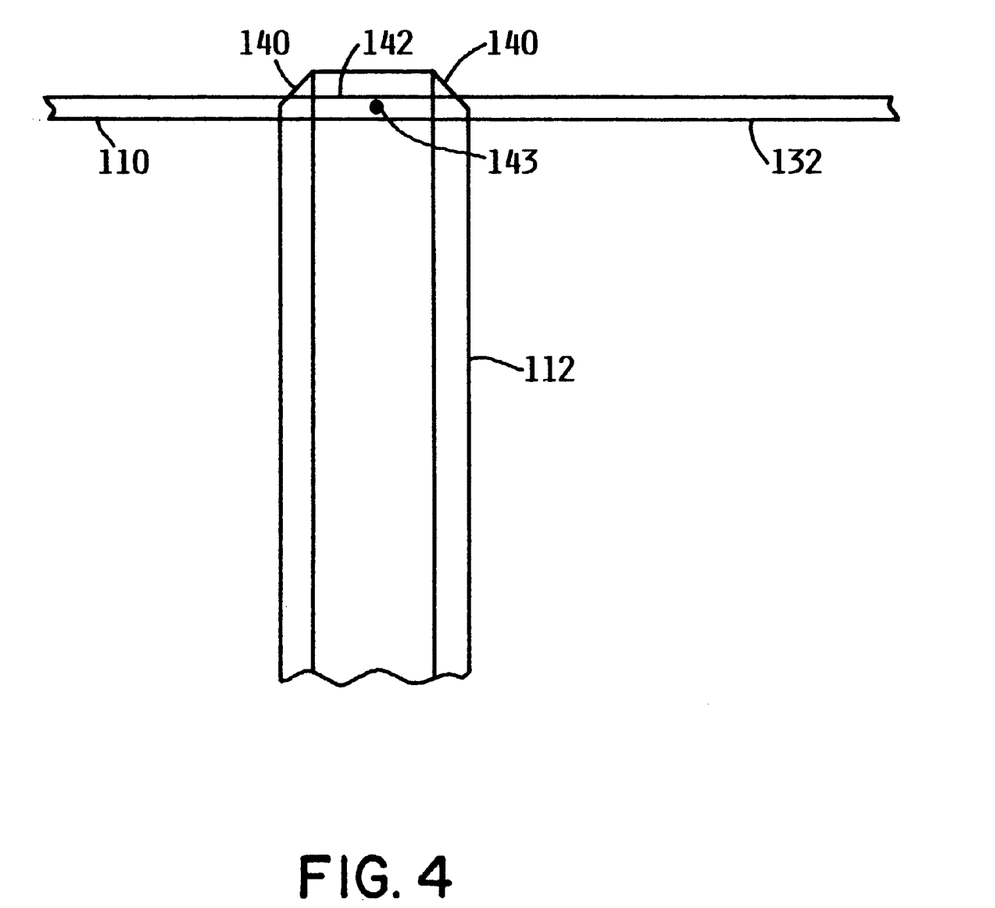
FIG. 4 is a side view of and edge portion of a disk transmitting a beam from the first embodiment of the inspection device of FIG. 1.

FIG. 3 shows a bottom view of a portion of the outer circumferential edge of disk 112 in the vicinity where beam 110, 132 is transmitted through intersection zone 142 (this would be the view of the disk from the vector indicated by arrow B in FIG. 1). FIG. 4 is a corresponding side view of the beam and disk. As shown in FIG. 3, beam 110 is not perpendicular to the major surfaces of disk 112, but rather intersects the surfaces at angle A, where angle A is preferably between 75 degrees and 80 degrees.

As shown in FIG. 4, disk 112 includes two chamfers 140. Intersection zone 142 (where the beam intersects the disk) passes partially through these chamfers 140. Also, it is noted that the optics are arranged so that the focal point of the electromagnetic beam 110 occurs at focal point 143, midway between the two major surfaces of disk 112. It is preferred to focus the beam midpoint between the surfaces of the disk, so that defects at either major surface, or in the chamfers associated with each major surface, will affect the beam in a roughly equal way. In this way, defects at either major surface of the disk can be detected with approximately equal accuracy and sensitivity.

As shown in FIG. 4, beam 110 preferably intersects disk 112 a little bit inwards of the outer circumferential edge of disk 112. In this embodiment, the beam intersects at approximately 150 $\mu$m from the outer edge, in the vicinity of the location where the 45 degree chamfer in the disk meets the major surfaces of the disk. Although the beam is not at the absolute outer circumferential edge of the disk, it is close enough to the outer circumferential edge of the disk so that any edge chips large enough to be considered defects will intersect the beam.

Since the beam intersects the disk close to its edge, it will not pick up defects at, for example, 1 mm inwards of the outer circumferential edge. As stated above, most conventional laser beam inspection devices, which can be used to complement the edge inspection of the present invention, do not inspect this portion of the disk because it is too close to the disk edge.

However, in this embodiment, the small gap in disk area between edge inspection by the present invention and any later disk surface inspection is not a great concern because the majority of defects in the transparent substrate generally occur at the inner or outer circumferential edge of the disk. If there is a concern about inspecting this intermediate area, there are several ways of handling this concern. For example, the beam could be directed to scan this area during subsequent rotations of the disk. As an alternative example, a wider beam could be used, and positioned to give coverage in this intermediate area.

Figure 5:
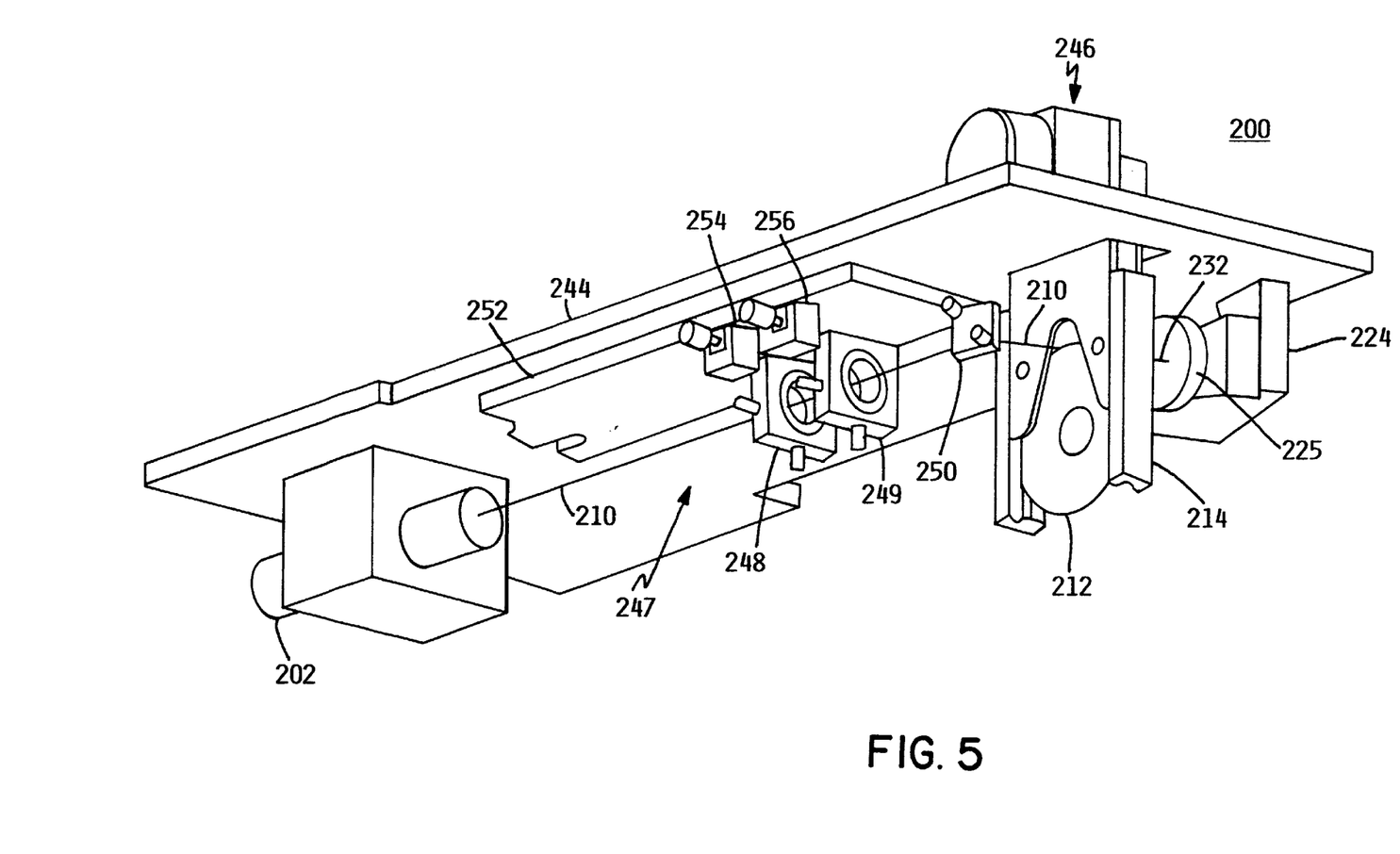
FIG. 5 is a perspective view of a second embodiment of an inspection device according to the present invention.

A second preferred embodiment of a disk inspection device 200 is shown in FIG. 5. One difference between inspection device 200 and previously-discussed inspection device 100 is that device 200 inspects only the outer circumferential edge of a disk, rather than both the outer and inner circumferential edges. Inspection device 200 may be preferred for applications where irregularities at the inner circumferential edge are not a concern. Disk inspection device 200 includes laser 202, focus assembly 247, mirror 250, rotation assembly 214, diaphragm 225, mobile detector 224, base 244, and drive motor 246.

Inspection device 200 is designed to inspect a glass disk 212 to be used as a hard disk drive in a computer, such as a server computer. For example, 84 mm diameter disks and 95 mm diameter glass disks are commonly used in hard disk drives.

According to one aspect of the present invention, the inspection of a transparent disk is performed prior to the time the recording medium, such as magnetic recording material, is applied to the disk. In this way, the transparent disk has not yet been rendered opaque by any applied recording medium. This inspection of a still-transparent disk is preferable because: (1) defects can be detected before incurring the expense of applying the recording medium; and (2) the inspection device can utilize transmitted electromagnetic radiation, which may yield a stronger more reliable signal than alternative embodiments that utilize scattered or reflected radiation.

Laser 202 is preferably a 1 mW Helium-Neon laser that puts out a beam 210 of visible light in the red range at a wavelength of 633 nm. Preferably, the beam is between 75 $\mu$m and 100 $\mu$m in diameter. Laser 202 and the other optical components are mounted to base 244. Based 244 is made of anodized aluminum and custom-made with conventional mounting hardware for mounting the various optical components at appropriate locations.

Focus assembly 247 includes converging lens 248, diverging lens 249, adjustment knob 254, adjustment knob 256 and rail 252. Beam 210 passes through diverging lens 248 and then converging lens 249. The diverging and converging lenses are used to control: (1) the quality of the light at the edges of the laser beam; (2) the diameter of beam 210; and (3) the location of the focal point of the beam, as discussed above in connection with FIG. 3.

Rail 252 and adjustment knobs 254 and 256 provide adjustability for focus assembly 247. Converging lens 248 can be precisely located along rail 252, in the direction of beam 210, by using adjustment knob 254. Similarly, converging lens 248 can be precisely located along rail 252, in the direction of beam 210, by using adjustment knob 254. Converging and diverging lenses 248, 249 can also be adjusted with respect to a plane perpendicular to beam 210 by conventional adjustment hardware provided with the respective lenses.

After passing through the lenses, beam 210 is reflected by mirror 250. Mirror 250 is held by an adjustable post (not shown) that allows fine adjustment of the location of mirror 250. Knobs on mirror 250 allow adjustment of the angular orientation of the plane of the mirror relative to the beam. By making small adjustments to mirror 250, beam 210 can be adjusted to intersect disk 212 at the desired distance from the circumferential edge and at the desired angle with respect to the major surfaces of the disk.

After reflection by mirror 250, beam 210 passes through transparent disk 212 in the vicinity of the outer circumferential edge of disk 212, and at an angle with respect thereto, as described above in connection with the embodiment of FIGS. 1 to 4. Similar to the embodiment of FIGS. 1 to 4, an intact outer circumferential edge will substantially transmit beam 210 as transmitted beam 232, while a chipped edge will scatter much of the beam 210, so that transmitted beam 232 is considerably weaker than beam 210.

Transmitted beam 232 next passes through diaphragm 225 and proceeds to mobile detector 224. Diaphragm 225 includes an adjustable iris. When the iris is enlarged by being opened more, more light can pass the diaphragm. When the iris is made smaller by being closed more, less light can pass the diaphragm. Diaphragm 225 protects mobile detector 224 from receiving scattered or ambient light, and can help adjust the sensitivity and facilitate calibration of mobile detector 224.

Mobile detector 224 is structured to detect visible light and therefore detects the amount of light present in transmitted beam 232. Mobile detector 224 is preferably a photodiode detector that is fast enough to detect a sufficient number of data points around the circumferential edge of the disk as the disk is rotated. Alternatively, other imaging hardware, such as a CCD camera could be used. Mobile detector 224 and diaphragm 225 can be precisely adjusted in space so that transmitted beam 232 reaches these components surely and squarely.

Disk 212 is constrained and driven by rotation assembly 214. Similar to the disk holder 114 of previously-described device 100, rotation assembly 214 constrains the disk between two drive wheels and one idler wheel (not separately shown in FIG. 5). The drive wheels are driven by drive motor 246. The drive wheels consequently drive disk 212 into rotation by friction. The idler wheel constrains the position of the disk while freely allowing the disk to rotate. Rotate assembly holds and rotates the disk without interfering with the path of beams.

In the preferred embodiment shown in FIG. 5, disk 212 is rotated at about 10 revolutions per minute. Mobile detector 224 samples transmitted radiation at a rate of about 3000 samples per second. The number of samples need to cover the outer circumference of a disk will depend on beam size and the circumference of the disk. Preferably, every point on the outer circumference is covered, with physical overlap in the intersection zones between consecutive samples. Although laser 202 of this embodiment is continuous, a pulsed laser could alternatively be used.

In this preferred embodiment, 6000 thousand data points are collected around the outer circumferential edge of disk 212. The data points are digitized and scaled such that a 0V reading yields a value of 0 and a 10V value yields a reading of 5. Once digitized and scaled, the 6000 data points in are put into an array labeled positionally 1 to 6000 (that is, the first point collected is 1 and the last 6000).

The detector employs an algorithm which takes the median of points 1 through 39 and compares that value to the value of point 20. Depending on the threshold set by the user, if point 20 deviates by the threshold (0.8% in this preferred embodiment) then it is registered as a defect. The next median is calculated between points 2 and 40 to determine if point 21 is "good" or "bad." This process continues around the disk.

A "bad" point does not necessarily indicate a defect. For example, an irregularity in the disk may be small enough to cause a few "bad" points, without being sufficiently large to render the disk useless for commercial purposes. Rather, a disk is preferably passed or failed based on the cumulative number of "bad" points around the entire disk, and/or based on too many consecutive "bad" points. For example, the user can set the cumulative "bad" point threshold to 20 points and the consecutive "bad" point threshold to 5. This means that if there are 20 or more "bad" points on the disk, then the disk fails (and will be discarded or recycled). Alternatively, if there are 5 or more "bad" points consecutively anywhere on the disk edge, then disk will also fail. Assuming that the diameter of the laser is 75 $\mu$m, 5 consecutive "bad" points would correlate with an irregularity of roughly 375 $\mu$m in size.

Figure 6:
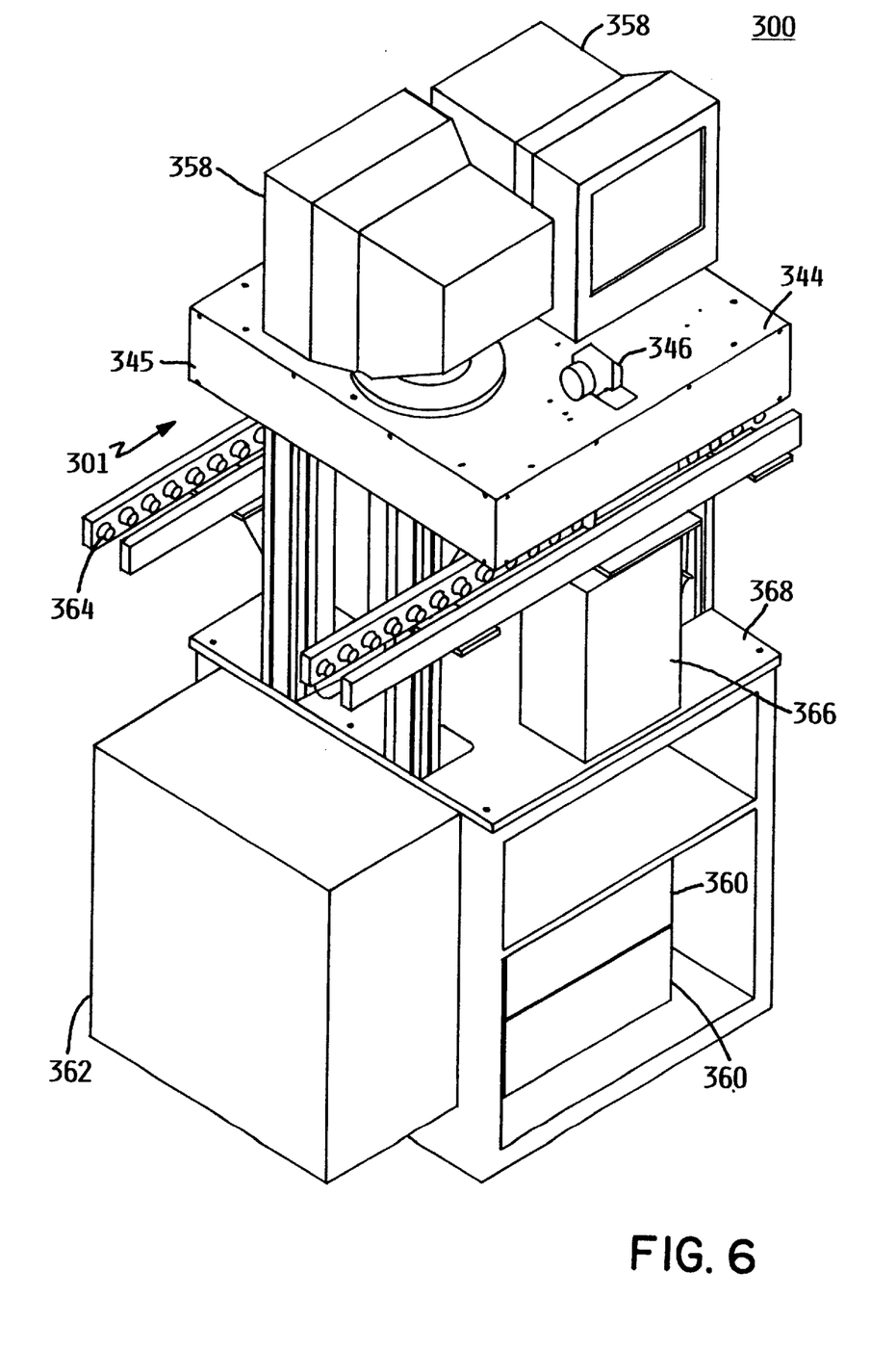
FIG. 6 is a perspective view of a third embodiment of an inspection device according to the present invention.

Disk inspection device 300 will now be described with reference to FIGS. 6 to 8. Disk inspection device 300 actually includes two independent inspection lines, so there are two of most components. Disk inspection device 300 includes two inspection assemblies 301, base 344, side guard 345, two drive motors 346 (one drive motor is visible in FIG. 6), two monitors 358, two personal computers 360, main power 362, two conveyors 364, two test heads 366 (only one is visible in FIG. 6) and platform 368.

Generally speaking, each inspection assembly 301 generates two beams. Each assembly sends its two beams through a disk in the vicinity of the inner and outer circumferential edges of the disk. The assemblies then detect the amount of laser radiation transmitted by the disk. Exemplary inspection assembly 301 will be described in more detail below with reference to FIGS. 6, 7 and 8.

Figure 8:
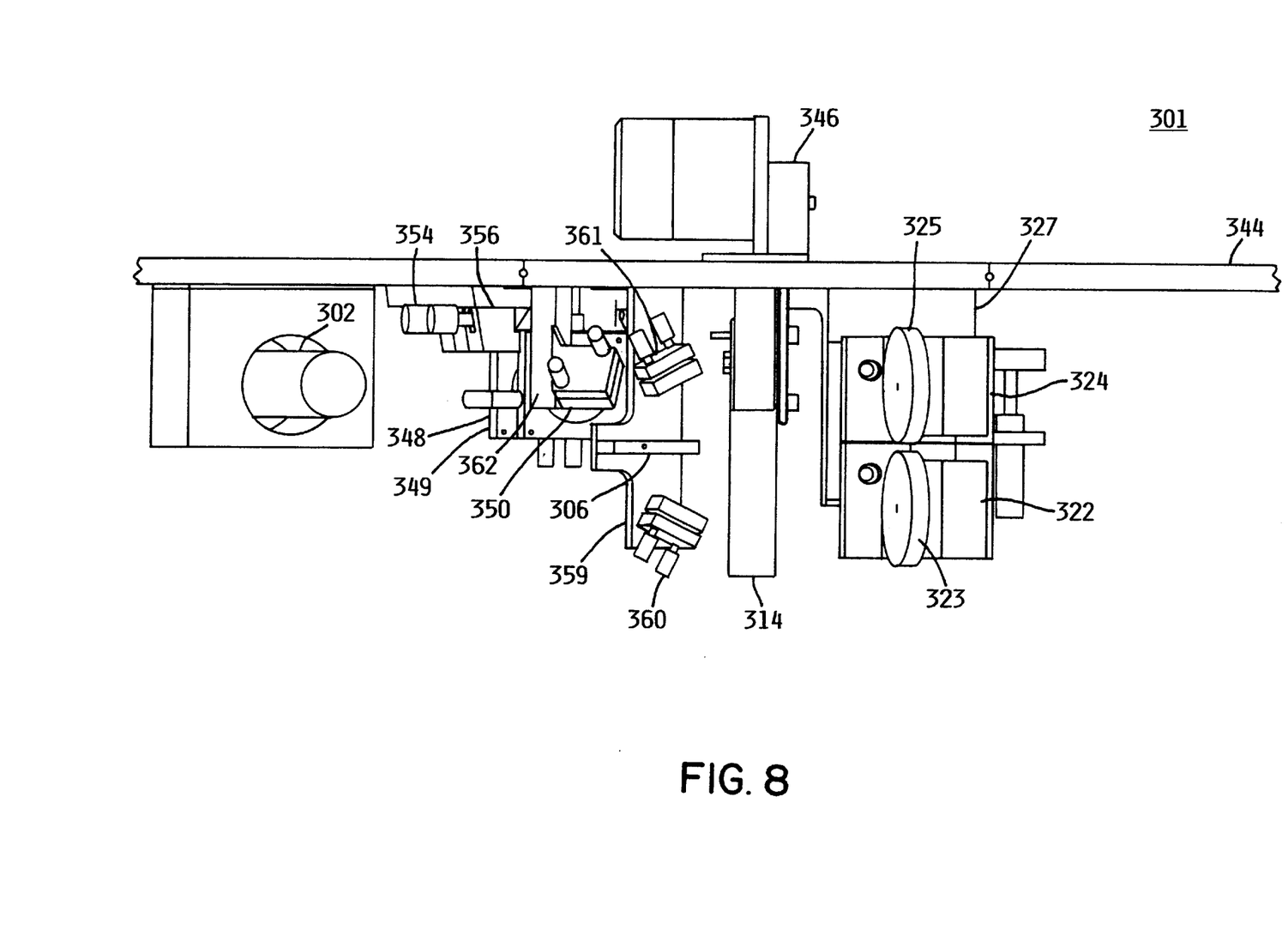
FIG. 8 is a side view of the third embodiment of FIG. 6.

Base 344 shown in FIG. 8 holds inspection assembly 301. Base 344 is equipped with side guard 346 to help keep ambient light away from inspection assembly 301 and to prevent inadvertent eye contact with the laser beam by inspection device operators. Platform 368 holds up the inspection assemblies 301, the monitors 358 and the test heads 366.

One monitor 358 and one personal computer 360 are associated with each of the two inspection lines. Personal computer 358 controls the operation of various components of the inspection assembly and receives and interprets transmitted-radiation data from the inspection assembly 301. Monitor 358 provides a visual display for computer 360. Printers, telephonic communication lines and other output devices could alternatively or additionally be provided for computers 360. Main power 362 is used to receive and route electrical power to various components of inspection device 300.

Conveyor 364 is structured to receive cassettes (not shown) holding disks for inspection. When the first disk of a cassette is aligned with test head 366, a Meran L-130 lifter blade inside of test head 366 pushes the disk up into the inspection assembly. When the inspection assembly 301 has finished its inspection, the lifter blade is lowered to allow the disk to descend back into the cassette. The cassette is then indexed forward disk-by-disk until every disk in the cassette has been inspected, and the disks with physical defects in their edges have been identified.

Inspection assembly 301 will now be discussed with reference to FIGS. 7 and 8. Inspection assembly 301 includes laser 302, focus assembly 347, primary mirror 350, beam splitter 306, bracket 359, first secondary mirror 360, second secondary mirror 361, rotation assembly 314, first mobile detector 322, first diaphragm 323, second mobile detector 324, second diaphragm 325 and translation stage 327.

Laser 302, focus assembly 347, primary mirror 350, rotation assembly 314, diaphragm 325 and mobile detector 324 are substantially similar to the corresponding components of previously-described inspection device 200 and will not be separately described here.

Figure 7:
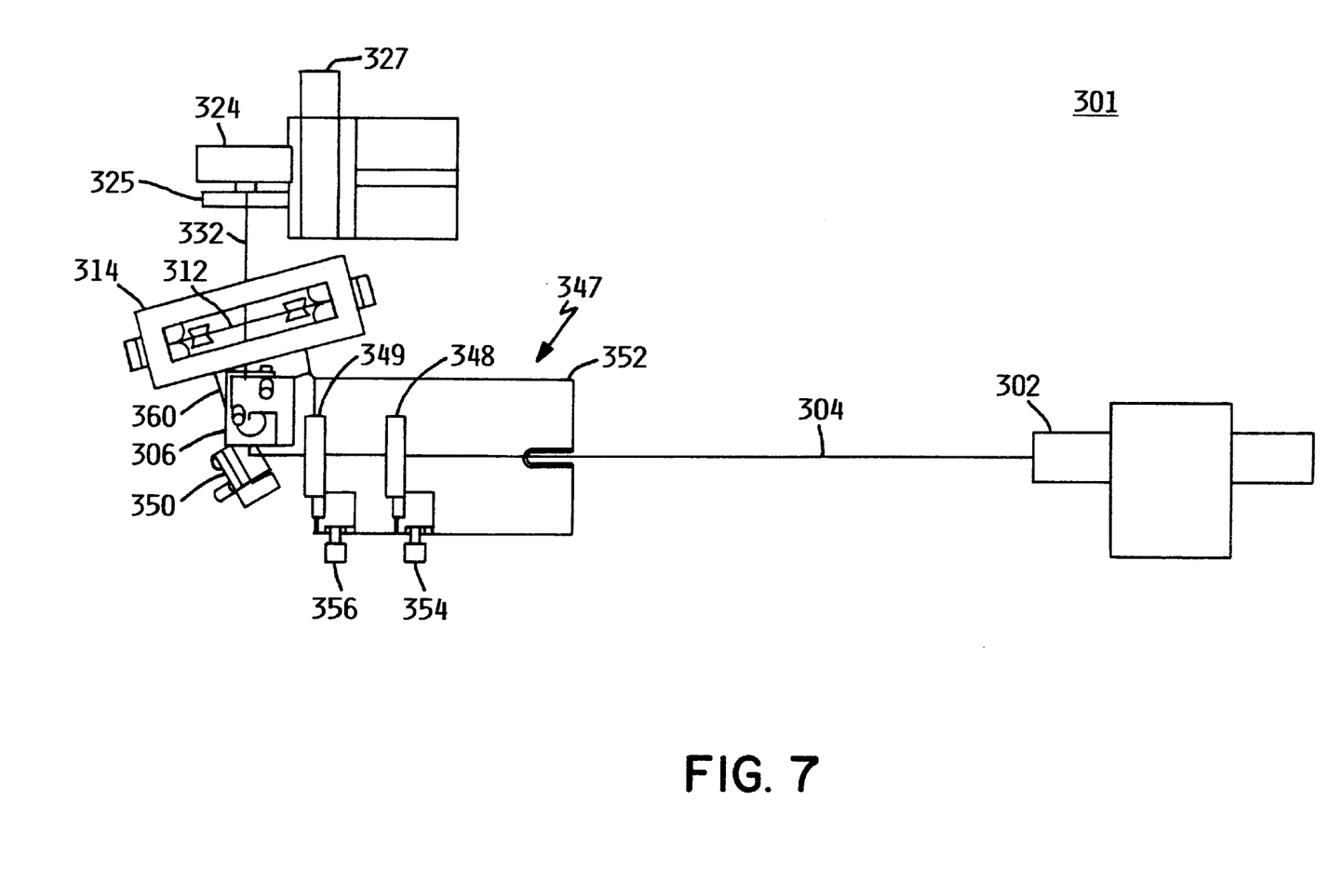
FIG. 7 is a bottom view of the third embodiment of FIG. 6.

Beam splitter 306 which splits laser beam 310 is a conventional laser beam splitter that splits the laser beam into two beams 332 (shown in FIG. 7 only). One beam 332 is subsequently directed to the outer circumferential edge of disk 312, while the other beam is subsequently directed to the inner circumferential edge of disk 312. More particularly, one beam emerges from beam splitter 306, and is reflected by first secondary mirror 360 toward an intersection zone at the outer circumferential edge of disk 312.

Disk 312 transmits this beam, at least in part, through first diaphragm 323 to first mobile detector 322. First mobile detector 322 determines the amount of transmitted radiation and sends this determination to personal computer 360 for evaluation as to whether the detected radiation is low enough to indicate a defect at the outer circumferential edge.

Similarly, another beam emerges from beam splitter 306, and is reflected by second secondary mirror 361 toward an intersection zone at the inner circumferential edge of disk 312. Disk 312 transmits this beam, at least in part, through second diaphragm 325 to second mobile detector 324. Second mobile detector 324 determines the amount of transmitted radiation and sends this determination to personal computer 360 for evaluation as to whether the detected radiation is low enough to indicate an edge chip at the inner circumferential edge.

Many variations on these preferred embodiments are possible. For example, the beam of radiation could enter the disk edgewise, rather than through a major surface. The same machine could be used to detect defects both at the disk edge as well as over the major surface of the disk. The beam could scan across the disk (for example, horizontally or vertically) rather than circumferentially. The disk could remain stationary while the beam scans around to edge locations on the disk.

While the present invention has been illustrated and described by means of a specific and embodiment, it is to be understood that numerous changes and modifications can be made therein without departing from the spirit and scope of the invention.

What is claimed is:

1. A disk inspection device for inspecting a disk having a circumferential edge, with the circumferential edge being subject to defects, the device comprising:

a beam generator structured to generate a beam of electromagnetic radiation;

a beam splitter that splits the beam produced by the beam generator into two distinct measurable beams, where a first beam is directed to intersect the surface of the disk at the inner circumferential edge near the mounting aperture and a second beam is directed to intersect the surface of the disk at the outer circumferential edge;

a disk holder structured to hold the disk, with the disk holder being located so that the two beams intersect the disk at an intersection zone, with the intersection zone being sufficiently close to the circumferential edge so that at least a portion of the intersection zone will overlap at least a portion of any defect located in the circumferential edge of the disk in the vicinity of the intersection zone; and a radiation detector structured and located to detect at least a portion of radiation from the beam after the beam has intersected the disk.

2. The device of claim 1 wherein the beam generator comprises a laser.

3. The device of claim 2 wherein the laser is a Helium-Neon laser that generates a beam of approximately 633 nm in wavelength and between 75 $\mu$m and 100 $\mu$m in diameter.

4. The device of claim 1 further comprising a mirror assembly wherein said assembly comprises a mirror surface positioned in the path of the beam between the beam generator and the intersection zone, said assembly reflecting at least a portion of the beam.

5. The device of claim 4 wherein the mirror assembly further comprises a device for adjusting the position of the mirror surface.

6. The device of claim 5 wherein the mirror surface is positioned so that the angle between the beam and a major surface of the disk is between 75 degrees and 80 degrees.

7. The device of claim 4 further comprising a base structured to mount the beam generator, the mirror assembly, the disk holder and the radiation detector.

8. The device of claim 1 wherein the disk holder comprises:
   a drive wheel structured to engage and drive the disk;
   an idler wheel structured to engage and support the disk; and
   a drive motor associated with the drive wheel, and structured to drive said drive wheel into rotation.

9. The device of claim 1 wherein the radiation detector comprises:
   a detector surface structured to detect radiation; and
   a detector adjustment device structured to adjust the position of the detector surface.

10. The device of claim 1 wherein the radiation detector comprises a computer structured to run an algorithm for determining whether a defect is present based on radiation detected by the radiation detector.

11. The device of claim 1 wherein the radiation detector is structured to run an algorithm for determining a defect by collecting detected radiation values at a plurality of points, determining a median value for the plurality of collected points, and ascribing an inspected point on the disk as defective when the detected radiation correlated with the inspected point is lower, by some predetermined amount, than the median value.

12. The device of claim 11 wherein the algorithm determines whether the disk fails the inspection based on the number and location of defective points over the disk.

13. The device of claim 12 wherein the beam generator and radiation detector are positioned so that the beam will pass through the disk, which is substantially transparent with respect to the beam, and so that at least a substantial portion of the beam will be transmitted through the disk to the radiation detector.

14. The device of claim 13 wherein the algorithm enables the detector to determine that a defect exists in the circumferential edge of the disk based on a decrease in detected radiation.

15. The device of claim 14 wherein the defect is determined based on a decrease in detected radiation at a plurality of points on the disk.

16. The device of claim 1 wherein the beam generator and the disk holder are positioned so that an angle between the beam and a major surface of the disk is between 90 degrees and 75 degrees.

17. The device of claim 16 wherein the angle is between 75 degrees and 80 degrees.

18. The device of claim 1 further comprising:
   a conveyer structured to transport disks to the vicinity of the disk holder; and
   a lifter blade movable between a first position and a second position for moving the disk into the disk holder and out of the disk holder.

19. A disk inspection device for inspecting a disk that is transparent to visible light and subject to defects, the device comprising:
   a Helium-Neon laser that generates a laser beam of approximately 633 nm in wavelength and between 75 $\mu$m and 100 $\mu$m in diameter.
   a beam splitter that splits the beam produced by the beam generator into two distinct measurable beams, where a first beam is directed to intersect the surface of the disk at the inner circumferential edge near the mounting aperture and a second beam is directed to intersect the surface of the disk at the outer circumferential edge;
   a disk holder comprising:
      a drive motor;
      a drive wheel that is driven to rotate by the drive motor; and
      an idler wheel, with the drive wheel and the idler wheel being structured and located so that an outer circumferential edge of the disk can be secured there between
   a mobile detector comprising:
      a detector surface structured and located to detect at least a portion of the laser beam; and
      instructions for determining whether a defect exists in the circumferential edge of the disk based on the detected radiation.
   a mirror assembly comprising:
      a mirror surface located in the path of the laser beam between the laser and the transparent disk and structured to reflect at least a substantial portion of the beam; and
      a mirror adjustment device for actuating the mirror surface to make fine adjustments to a position of the mirror surface.

20. A method of detecting chips in a circumferential edge of a disk, the method comprising the steps of:
   generating a beam of electromagnetic radiation;
   spliting the generated beam into two distinct measurable beams,
   directing the beam that intersects the surface of the disk at the inner circumferential edge near the mounting aperture and directing a second beam to intersect the surface of the disk at the outer circumferential edge;
   detecting radiation from the beam after it has intersected the disk; and
   determining the presence of a chip based on the amount of radiation detected at the detecting step.

* * * * *